United States Patent [19]
Behr et al.

[11] Patent Number: 5,616,794
[45] Date of Patent: Apr. 1, 1997

[54] PROCESS FOR PREPARING FLUOROCARBOXYLIC ACID HALIDES

[75] Inventors: Frederick E. Behr; Yuri Cheburkov, both of Woodbury, Minn.

[73] Assignee: Minnesota Mining and Manufacturing Company, St. Paul, Minn.

[21] Appl. No.: 558,243

[22] Filed: Nov. 17, 1995

[51] Int. Cl.$^6$ .................................................... C07C 51/58
[52] U.S. Cl. .......................................................... 562/851
[58] Field of Search ............................................. 562/851

[56] References Cited

U.S. PATENT DOCUMENTS

| | | |
|---|---|---|
| 2,732,398 | 1/1956 | Brice et al. . |
| 2,765,326 | 10/1956 | Severson et al. . |
| 2,950,317 | 8/1960 | Brown et al. . |
| 2,951,051 | 8/1960 | Tiers . |
| 3,555,100 | 1/1971 | Garth et al. . |
| 3,689,545 | 9/1972 | Hahn et al. . |
| 3,723,485 | 3/1973 | Thom . |
| 3,824,197 | 7/1974 | Smith et al. . |
| 3,824,198 | 7/1974 | Smith et al. . |
| 3,824,219 | 7/1974 | Smith et al. . |
| 3,824,220 | 7/1974 | Smith et al. . |
| 4,318,867 | 3/1982 | Yamabe . |
| 4,400,325 | 8/1983 | von Werner et al. . |

FOREIGN PATENT DOCUMENTS

| | | |
|---|---|---|
| 251567 | 11/1970 | U.S.S.R. . |
| 776507 | 6/1957 | United Kingdom . |
| 2052501 | 1/1981 | United Kingdom . |

OTHER PUBLICATIONS

T. Abe et al., *Preparation, Properties, and Industrial Applications of Organofluorine Compounds*, R. E. Banks (editor), John Wiley & Sons, pp. 24–28 and 37–39, New York, (1982).

P. W. Trott et al., 126th National Meeting of American Chemical Society, abstract at p. 42–M, New York, NY (1954).

P. J. Stang et al., Synthesis 1982, 85.

R. N. Haszeldine et al., J. Chem. Soc. 1955, 2901.

Coffman & Raasch, J. Org. Chem. 14, 747 (1949).

H. Weiyuan et al., Chemistry 2, 31 (1987).

W. Y. Huang, J. Fluorine Chem. 32, 179 (1986).

Comninellis et al., "Direct Conversion of Alkylthiols to the Corresponding Sulfonyl Fluorides", Synthesis 1974, 887.

Davies et al., "Aliphatic Sulphonyl Fluorides", J. Chem. Soc. 1932, 483.

Behr et al., "Hydrolysis of F–Octanesulfinic Acid", 11th International Symposium on Fluorine Chemistry, Aug. 5–9, 1985, Abstracts, p. 101..

Hu et al., "Reaction of Perfluoroalkanesulfinates with Allyl and Propargyl Halides. A Convenient Synthesis of 3–(Pefluoroalkyl)prop–1–enes and 3–(Perfluoroalkyl)allenes", J. Org. Chem. 1991, 56, pp. 2801–2804.

Hauptschein et al., "Fluorocarbon Halosulfates and a New Route to Fluorocarbon Acids and Derivatives, I. Polyfluoroalkyl Chlorosulfates", J. Am. Chem. Soc., 83, 2500 (1961).

Hu et al., "The Pyrolysis of 3–Oxa–11–Chloro–Eicosafluoroundecane Sulfinate and Sulfonate Salts", J. of Fluorine Chemistry, 37 (1987) 337–342.

Huang et al., "Studies on Deiodo–Sulfination Part, II. The Reactions of Perfluoroalkanesulfinates with Halogen and Halogen Acids and a New Method for the Synthesis of Perfluorosulfonic Acid", J. of Fluorine Chemistry, 23 (1983) 229–240.

Huang et al., "Studies on Deiodo–Sulfination. Part I. Studies on the Deiodo–Sulfination of Perfluoroalkyl Iodides", J. of Fluorine Chemistry, 23 (1983) 193–204.

Hu et al., "Photooxidation of Perhalofluorosulfinates. A Simple and Effective Method for the Synthesis of Perhalofluorocarboxylic Acids and Their Esters from the Corresponding Sulfonyl Fluorides", J. of Fluorine Chemistry, 42 (1989) 145–148.

Hu et al., "Reaction of Perhalofluoroalkyl Sulfinates With One–Electron Transfer Oxidants. A Facile Method For the Synthesis of Perhalofluorocarboxylic Acids", J. of Fluorine Chemistry 49 (1990) 433–437.

Howells et al., "Trifluoromethanesulfonic Acid and Derivatives", Chemical Reviews, 77, No. 1, 89 (1977).

Huang et al., "The Reaction of Sodium Perfluoroalkanesulfinate with PCl", Chinese Chemical Letters vol. 1, No. 1, pp. 27–28, 1990.

Olah et al., "The Simple Practical Preparation of Trifluoromethyl Trifluoromethanesulfonate (Triflate)", Synthesis, Communications, pp. 319–320, May 1976.

*Primary Examiner*—Paul J. Killos
*Attorney, Agent, or Firm*—Gary L. Griswold; Walter N. Kirn; Lucy C. Weiss

[57] ABSTRACT

A process for preparing fluorocarboxylic acid halides comprises the steps of (a) forming a starting composition comprising (i) at least one fluorosulfonic acid halide comprising at least one halosulfonyldifluoromethyl group ($-CF_2SO_2X$, wherein X is halogen); and (ii) at least one Group III or Group V Lewis acid; and (b) allowing the fluorosulfonic acid halide and the Lewis acid to react to form a product composition comprising at least one fluorocarboxylic acid halide. The process enables the preparation of even higher molecular weight fluorocarboxylic acid halides in good yield.

16 Claims, No Drawings

PROCESS FOR PREPARING FLUOROCARBOXYLIC ACID HALIDES

FIELD OF THE INVENTION

This invention relates to processes for preparing fluorinated carboxylic acid halides.

BACKGROUND OF THE INVENTION

Many products of commercial value (such as oil- and water-repellent finishes for textiles, paper, electronic articles, and the like; stain-repellent finishes for leather; and surfactants for a variety of applications) can be made from fluorocarboxylic acid halides. Fluorocarboxylic acid fluorides can be prepared from telomers of tetrafluoroethylene followed by appropriate oxidation, but a characteristic of this method is that a distribution of molecular weights is obtained.

Fluorocarboxylic acid fluorides can also be prepared by electrochemical fluorination (ECF) of the corresponding hydrocarbon carboxylic acid (or a derivative thereof), using either anhydrous hydrogen fluoride (Simons ECF) or KF·2HF (Phillips ECF) as the electrolyte. However, a drawback of Simons ECF is that side reactions often occur, and low purity and low yields (particularly at higher molecular weights) are often obtained due to the formation of rearrangement and degradation products. (See, e.g., the discussion by T. Abe et al. in *Preparation, Properties, and Industrial Applications of Organofluorine Compounds*, edited by R. E. Banks, John Wiley & Sons, pages 24–28, New York (1982).)

Although Phillips ECF (KF·2HF) or direct fluorination ($F_2$) can be employed to reduce the occurrence of side reactions and provide high yields of a desired fluorinated product, higher molecular weight hydrocarbon carboxylic acids cannot be fluorinated by such techniques without undergoing decarboxylation and/or other side reactions. Hydrocarbon carboxylic acid halides are extremely water-sensitive and difficult to handle, and hydrocarbon carboxylic acid chlorides yield chlorine-substituted fluorochemical products.

Thus, improved routes to fluorocarboxylic acid halides are highly desired in the art.

SUMMARY OF THE INVENTION

Briefly, this invention provides a process for preparing fluorocarboxylic acid halides. The process comprises the steps of (a) forming a starting composition comprising (i) at least one fluorosulfonic acid halide (e.g., perfluorooctanesulfonyl fluoride) comprising at least one halosulfonyldifluoromethyl group ($-CF_2SO_2X$, wherein X is halogen); and (ii) at least one Group III or Group V Lewis acid (e.g., antimony pentafluoride); and (b) allowing the fluorosulfonic acid halide and the Lewis acid to react to form a product composition comprising at least one fluorocarboxylic acid halide. Preferably, the fluorosulfonic acid halide is a perfluoroalkanesulfonic acid fluoride, and the Lewis acid is antimony pentafluoride or aluminum chloride.

Surprisingly, the process of the invention enables the formation and retention of the carbonyl halide moiety and provides higher yields of fluorocarboxylic acid fluorides than can be obtained by the Simons ECF of hydrocarbon carboxylic acids (or derivatives thereof). Even higher molecular weight fluorocarboxylic acid halides can be prepared in good yield in a simple, one-step process.

Furthermore, the process utilizes fluorosulfonic acid fluorides which, unlike fluorocarboxylic acid fluorides, can be effectively prepared in good yields (even at higher molecular weights) by the Simons ECF of readily available starting materials.

DETAILED DESCRIPTION OF THE INVENTION

Fluorosulfonic acid halides suitable for use in the process of the invention are those which contain at least one halosulfonyldifluoromethyl group. A class of useful compounds is that which can be represented by the general formula (I) below:

$$R_f\!-\!CF_2SO_2X \qquad (I)$$

wherein $R_f$ is selected from the group consisting of perfluorinated alkyl groups having from 1 to about 11 carbon atoms, partially-fluorinated alkyl groups having from 1 to about 11 carbon atoms, unsubstituted or perfluoroalkyl-substituted perfluorocycloalkyl groups having from 4 to about 8 (preferably, 5 to 6) carbon atoms, and unsubstituted or perfluoroalkyl-substituted, partially-fluorinated cycloalkyl groups having from 4 to about 8 (preferably, 5 to 6) carbon atoms; and X is selected from the group consisting of fluorine and chlorine. Preferably, X is fluorine and $R_f$ is perfluoroalkyl (more preferably, perfluoroalkyl having from about 3 to about 7 carbon atoms).

Fluorosulfonic acid fluorides (and indirectly, the chlorides) can be prepared by the Simons ECF of hydrocarbon sulfonic acid halides, as described by T. Abe et al. in *Preparation, Properties, and Industrial Applications of Organofluorine Compounds*, R. E. Banks (editor), pages 37–39, John Wiley & Sons, New York (1982). The hydrocarbon sulfonic acid halide precursors can be prepared by oxidative chlorination of a mercaptan followed by, if desired, exchange with fluoride ion (as described, e.g., by Davies et al. in J. Chem. Soc. 1932, 483) or by direct conversion of alkylthiols to the corresponding sulfonyl fluorides using nitrogen dioxide (as described, e.g., by Comninellis et al. in Synthesis 1974, 887).

In particular, perfluoroalkanesulfonic acid fluorides (and, indirectly, the chlorides) are readily available by the electrochemical fluorination of the corresponding alkanesulfonic acid fluorides, as described in U.S. Pat. No. 2,732,398 (Brice et al.), the description of which is incorporated herein by reference. (See also P. W. Trott et al., 126th National Meeting of the American Chemical Society, abstract at page 42-M, New York, N.Y. (1954).) Perfluorooctanesulfonyl fluoride is commercially available from 3M Co. under the tradename Fluorad™ fluorochemical sulfonyl fluoride FX-8.

Routes to perfluoroalkanesulfonic acid chlorides are described by P. J. Stang et al. in Synthesis 1982, 85 and by R. N. Haszeldine et al. in J. Chem. Soc. 1955, 2901. The chlorides of the ω-hydrofluorinated acids are described by Coffman and Raasch in J. Org. Chem. 14, 747 (1949), by H. Weiyuan et al. in Chemistry 2, 31 (1987), and by W. Y. Huang, J. Fluorine Chem. 32, 179 (1986). See also the method described in U.S. Pat. No. 2,950,317 (Brown et al.) the description of which is incorporated herein by reference.

Representative examples of fluorosulfonic acid halides suitable for use in the process of the invention include $C_2F_5SO_2F$, $C_2F_5SO_2Cl$, $C_4F_9SO_2F$, $C_4F_9SO_2Cl$, $C_8F_{17}SO_2F$, $C_8F_{17}SO_2Cl$, $FSO_2(CF_2)_4SO_2F$, $C_{10}F_{21}SO_2F$, $C_{10}F_{21}SO_2Cl$, cyclo-$(C_6F_{11})CF_2SO_2F$, cyclo-$(C_6F_{11})CF_2SO_2Cl$, $C_2F_5$-cyclo-$(C_6F_{10})CF_2SO_2F$, $C_2F_5$-cyclo-$(C_6F_{10})CF_2SO_2Cl$, $H(CF_2)_2SO_2Cl$, $H(CF_2)_4SO_2Cl$, $H(CF_2)_8SO_2Cl$, $H(CF_2)_{10}SO_2Cl$, $H(CF_2)_4SO_2F$, $H(CF_2)_8SO_2F$, cyclo-$(C_6F_{10}H)CF_2SO_2F$, cyclo-$(C_6F_{10}H)CF_2SO_2Cl$, $C_2F_5$-cyclo-$(C_6F_9H)$-$CF_2SO_2F$, and $C_2F_5$-cyclo-$(C_6F_9H)CF_2SO_2Cl$. Preferably, perfluoroalkanesulfonic acid fluorides and chlorides are utilized, most preferably, perfluorooctanesulfonyl fluoride and perfluorobutanesulfonyl fluoride because of their high yields from the electrochemical fluorination process and correspondingly low costs (see, e.g., T. Abe et al., supra, page 37).

Lewis acids suitable for use in the process of the invention are those which comprise Group III or Group V elements. Such compounds can be prepared by known methods, and many are commercially available. Generally, the Lewis acids can be of sufficient strength to cleave the carbon-sulfur bond of the fluorosulfonic acid halide. Representative examples of suitable Lewis acids include $SbF_5$, $AlCl_3$, $AlBr_3$, and $AsF_5$, all of which are commercially available. Preferred Lewis acids are $SbF_5$ and $AlCl_3$, with $AlCl_3$ being most preferred.

The process of the invention can be carried out by introducing to a vessel a starting composition comprising (preferably, consisting essentially of) at least one fluorosulfonic acid halide and at least one Group III or Group V Lewis acid. The vessel can be made of glass or other corrosion-resistant material and is preferably connected to a suitable condensing system (e.g., condenser (s) and/or trap (s)) for collecting volatile reaction products. Preferably, the vessel is also equipped with a suitable mechanical agitator, and, optionally, with a scrubber to remove gaseous inorganic by-products. The fluorosulfonic acid halide and Lewis acid starting materials can be introduced to the vessel separately or in combination, and in any order. The starting materials and the vessel should preferably be substantially dry, and substantially anhydrous conditions should preferably be maintained to avoid hydrolysis of the Lewis acid starting material. Inert diluent(s), e.g., perfluorohexane or perfluorooctane, can be utilized, if desired, but are not generally required.

The process of the invention can generally be carried out by heating the contents of the vessel (at a temperature in the range of from about 20° C. to about 150° C., preferably, from about 80° C. to about 100° C., and at pressures equal to or greater than atmospheric) preferably with agitation, until evolution of gas ceases (e.g., from about 2 to about 4 hours). The fluorosulfonic acid halide and Lewis acid starting materials can be utilized in mole ratios of from about 1:1 to about 10:1 (acid halide:acid), preferably from about 4:1 to about 7:1, most preferably in a ratio of about 5:1. Both the reaction conditions and the proportions of starting materials can vary widely.

The process of the invention can be carried out continuously (e.g., by continuously feeding a starting composition to the vessel and continuously withdrawing a product composition from the vessel), semi-continuously (e.g., by continuously feeding a starting composition and intermittently withdrawing a product composition, or by intermittently feeding a starting composition and continuously withdrawing a product composition), or batchwise. The desired fluorocarboxylic acid halide products of the process of the invention (as well as by-products such as, e.g., fluoroalkanes) can be recovered from a product composition by conventional separation means, e.g., by decantation, distillation, extraction, chromatography, or adsorption. Any unreacted fluorosulfonic acid halide starting material can also be recovered similarly and then recycled, if desired.

The process of the invention provides higher yields of fluorocarboxylic acid fluorides than can be obtained by the Simons ECF of hydrocarbon carboxylic acids (or derivatives thereof). Even higher molecular weight fluorocarboxylic acid halides can be prepared in good yield in a simple, one-step process. Fluorocarboxylic acid halides are useful in the preparation of many products of commercial value (such as oil- and water-repellent finishes for textiles, paper, electronic articles, and the like; strain-repellent finishes for leather; and surfactants for a variety of applications).

Objects and advantages of this invention are further illustrated by the following examples, but the particular materials and amounts thereof recited in these examples, as well as other conditions and details, should not be construed to unduly limit this invention.

EXAMPLES

EXAMPLE 1

Reaction of Perfluorooctanesulfonyl Fluoride and Antimony Pentafluoride

A round bottom flask, equipped with a reflux condenser, a −78° C. cold trap, and a magnetic stir bar, was charged with perfluorooctanesulfonyl fluoride (4.1 g, 8.2 mmol) and antimony pentafluoride (0.4 g, 0 1.8 mmol) and was heated to 100° C. for 2.5 hours with stirring. Initially the resulting mixture was homogeneous, but two separate phases developed as the reaction progressed. The colorless, transparent upper layer (3.61 g) was separated from the lower layer. Gas chromatographic analysis of the upper layer showed the following components: perfluorooctanoyl fluoride (24 area %), perfluorooctane (36 area %), and unreacted perfluorooctanesulfonyl fluoride starting material (39 area %). The contents of the cold trap was analyzed by gas chromatography/Fourier transform infrared spectroscopy (GC/FTIR) and determined to be a mixture of $SOF_2$ and $SO_2$.

EXAMPLE 2

Reaction of Perfluorooctanesulfonyl Fluoride and Antimony Pentafluoride

Using essentially the procedure of Example 1, perfluorooctanesulfonyl fluoride (10.1 g, 20 mmol) and antimony pentafluoride (0.66 g, 3 mmol) were combined and heated to 105°–110° C. for 3 hours. The resulting mixture was then distilled, and the fraction (8.3 g) boiling up to 106° C. was collected. Gas chromatographic analysis of the collected fraction showed the following components: perfluorooctanoyl fluoride (24 area %), perfluorooctane (65 area %), and unreacted perfluorooctanesulfonyl fluoride starting material (9 area %).

EXAMPLE 3

Reaction of Perfluorooctanesulfonyl Fluoride and Antimony Pentafluoride

Using essentially the procedure of Example 1, perfluorooctanesulfonyl fluoride (5.0 g, 9.9 mmol) and antimony pentafluoride (0.64 g, 2.9 mmol) were combined 0 and heated to 98° C. for 1 hour. Gas chromatographic analysis of the resulting mixture showed the following components: perfluorooctanoyl fluoride (27 area %), perfluorooctane (56 area %), and unreacted perfluorooctanesulfonyl fluoride starting material (15 area %). An additional 5.0 g of perfluorooctanesulfonyl fluoride was added to the mixture, and the resulting mixture was heated at 110° C. for four hours.

Gas chromatographic analysis of the mixture then revealed 18 area % perfluorooctanesulfonyl fluoride starting material. Five additional grams of the sulfonyl fluoride was added to the mixture, and the resulting mixture was refluxed at 125° C. for 16 hours. The resulting upper layer (12.6 g) was separated from the lower, dark, viscous layer and was distilled from 0.2 g of NaF, collecting the fraction in the range of 102°–108° C. (10.3 g). Gas chromatographic analysis of the collected fraction showed the following components: perfluorooctanoyl fluoride (27 area %), perfluorooctane (67 area %), and unreacted perfluorooctanesulfonyl fluoride starting material (6 area %).

EXAMPLE 4

Reaction of Perfluorooctanesulfonyl Fluoride and Aluminum Chloride

Using essentially the procedure of Example 1, perfluorooctanesulfonyl fluoride (4.0 g, 8.0 mmol) and aluminum chloride (1.0 g, 8.0 mmol) were combined and heated to 100°–110° C. for five hours. The resulting mixture was distilled, and the fraction boiling at 50°–86° C. at 30 torr was collected (1.83 g). Gas chromatographic analysis of the collected fraction showed the following components: perfluorooctanoyl chloride (13 area %), perfluorooctane (9 area %), 1-chloro-perfluorooctane (23 area %), and perfluorooctanesulfonyl chloride (56 area %).

EXAMPLE 5

Reaction of Perfluorooctanesulfonyl Fluoride and Boron Trifluoride

A dry 180 mL Hastelloy™ B pressure reactor equipped with a mechanical stirrer was charged with perfluorooctanesulfonyl fluoride (51 g, 0.11 mol), was sealed, was cooled with solid carbon dioxide, and was attached to a vacuum pump to further reduce the internal pressure. Anhydrous gaseous boron trifluoride (8 g, 0.12 mol) was added to the reactor, and the reactor was then heated at 140° C. for 16 hours with stirring. The reactor was cooled, and the excess boron trifluoride pressure was vented to a scrubber filled with potassium hydroxide. The remaining clear fuming liquid (49.5 g) from the reactor was analyzed by gas chromatography (GC). No low boiling components were detected. Only unreacted perfluorooctanesulfonyl fluoride starting material was detected by GC analysis.

EXAMPLE 6

Reaction of Perfluorooctanesulfonyl Chloride and Antimony Pentafluoride

Using essentially the procedure of Example 1, perfluorooctanesulfonyl chloride (5.74 g, 11 mmol) and antimony pentafluoride (0.47 g, 2 mmol) were combined and heated to 100°–130° C. for four hours. The resulting upper layer (4.96 g) was separated from precipitated antimony halides on the bottom. Gas chromatographic analysis of the separated upper layer showed the following components: perfluorooctanoyl fluoride (27 area %), perfluorooctane (37 area %), perfluorooctanesulfonyl fluoride (16 area %), and unreacted perfluorooctanesulfonyl chloride starting material (18 area %).

Various modifications and alterations of this invention will become apparent to those skilled in the art without departing from the scope and spirit of this invention.

We claim:

1. A process for preparing fluorocarboxylic acid halides comprising the steps of (a) forming a starting composition comprising (i) at least one fluorosulfonic acid halide comprising at least one halosulfonyldifluoromethyl group; and (ii) at least one Group III or Group V Lewis acid; and (b) allowing said fluorosulfonic acid halide and said Lewis acid to react to form a product composition comprising at least one fluorocarboxylic acid halide.

2. The process of claim 1 wherein said fluorosulfonic acid halide is a perfluoroalkanesulfonic acid fluoride.

3. The process of claim 1 wherein said fluorosulfonic acid halide is represented by the general formula $$R_f\text{—}CF_2\text{—}SO_2X \qquad (I)$$

wherein $R_f$ is selected from the group consisting of perfluorinated alkyl groups having from 1 to about 11 carbon atoms, partially-fluorinated alkyl groups having from 1 to about 11 carbon atoms, unsubstituted or perfluoroalkyl-substituted perfluorocycloalkyl groups having from 4 to about 8 carbon atoms, and unsubstituted or perfluoroalkyl-substituted, partially-fluorinated cycloalkyl groups having from 4 to about 8 carbon atoms; and X is selected from the group consisting of fluorine and chlorine.

4. The process of claim 3 wherein said $R_f$ is a perfluorinated alkyl group.

5. The process of claim 4 wherein said perfluorinated alkyl group has from about 3 to about 7 carbon atoms.

6. The process of claim 3 wherein said X is fluorine.

7. The process of claim 1 wherein said fluorosulfonic acid halide is selected from the group consisting of perfluorooctanesulfonyl fluoride, perfluorooctanesulfonyl chloride, and perfluorobutanesulfonyl fluoride.

8. The process of claim 7 wherein said fluorosulfonic acid halide is perfluorooctanesulfonyl fluoride.

9. The process of claim 1 wherein said starting composition consists essentially of (i) at least one fluorosulfonic acid halide comprising at least one halosulfonyldifluoromethyl group; and (ii) at least one Group III or Group V Lewis acid.

10. The process of claim 1 wherein said Lewis acid is of sufficient strength to cleave the carbon-sulfur bond of said fluorosulfonic acid halide.

11. The process of claim 1 wherein said Lewis acid is selected from the group consisting of $SbF_5$, $AlCl_3$, $AlBr_3$, and $AsF_5$.

12. The process of claim 11 wherein said Lewis acid is selected from the group consisting of $SbF_5$ and $AlCl_3$.

13. The process of claim 12 wherein said Lewis acid is $AlCl_3$.

14. The process of claim 1 wherein said fluorosulfonic acid halide and said Lewis acid are utilized in mole ratios of from about 1:1 to about 10:1.

15. The process of claim 1 further comprising the step of recovering said fluorocarboxylic acid halide from said product composition.

16. A process for preparing fluorocarboxylic acid halides comprising the steps of (a) forming a starting composition comprising (i) at least one perfluoroalkanesulfonic acid fluoride; and (ii) at least one Lewis acid selected from the group consisting of aluminum chloride and antimony pentafluoride; and (b) allowing said perfluoroalkanesulfonic acid fluoride and said Lewis acid to react to form a product composition comprising at least one fluorocarboxylic acid halide.

* * * * *